United States Patent
Chen et al.

(10) Patent No.: US 12,319,687 B2
(45) Date of Patent: Jun. 3, 2025

(54) INDOLE ALKALOID COMPOUND IN NONI ENZYME AND PREPARATION METHOD AND APPLICATION THEREOF

(71) Applicant: HAINAN NORMAL UNIVERSITY, Haikou (CN)

(72) Inventors: Guangying Chen, Haikou (CN); Bin Zhang, Haikou (CN); Xiaobao Li, Haikou (CN); Ting Zhao, Haikou (CN); Kelei Huang, Haikou (CN); Hao Wang, Haikou (CN)

(73) Assignee: HAINAN NORMAL UNIVERSITY, Hainan (CN)

( * ) Notice: Subject to any disclaimer, the term of this patent is extended or adjusted under 35 U.S.C. 154(b) by 890 days.

(21) Appl. No.: 17/593,643

(22) PCT Filed: Mar. 22, 2021

(86) PCT No.: PCT/CN2021/082001
§ 371 (c)(1),
(2) Date: Sep. 22, 2021

(87) PCT Pub. No.: WO2022/141820
PCT Pub. Date: Jul. 7, 2022

(65) Prior Publication Data
US 2023/0174527 A1 Jun. 8, 2023

(30) Foreign Application Priority Data
Dec. 28, 2020 (CN) .......................... 202011572513.1

(51) Int. Cl.
*C07D 471/04* (2006.01)
(52) U.S. Cl.
CPC ........ *C07D 471/04* (2013.01); *C07B 2200/07* (2013.01)
(58) Field of Classification Search
CPC ................................................... C07D 471/04
See application file for complete search history.

(56) References Cited

FOREIGN PATENT DOCUMENTS

WO WO-2009073620 A2 * 6/2009 ........... A61K 31/138

OTHER PUBLICATIONS

Chang A., Jeske L., Ulbrich S., Hofmann J., Koblitz J., Schomburg I., Neumann-Schaal M., Jahn D., Schomburg D. Brenda, the Elixir core data resource in 2021: new developments and updates. (2021), Nucleic Acids Res., 49:D498-D508.*
'Enzymes' in IUPAC Compendium of Chemical Terminology, 3rd ed. International Union of Pure and Applied Chemistry; 2006. Online version 3.0.1, 2019.*

* cited by examiner

*Primary Examiner* — David K O'Dell
(74) *Attorney, Agent, or Firm* — JEEN IP LAW, LLC

(57) ABSTRACT

Provided are indole alkaloid compounds in a noni enzyme, wherein the structural formula is shown in the following formula:

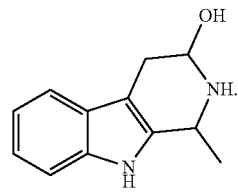

Provided is a preparation method of the above-mentioned compound and application of the indole alkaloid compound in the noni enzyme in the preparation of an α-glucosidase inhibitor. The indole alkaloid compound in the noni enzyme provided by the invention has a simple preparation process, low cost and abundant raw material sources.

6 Claims, 2 Drawing Sheets

INDOLE ALKALOID COMPOUND IN NONI ENZYME AND PREPARATION METHOD AND APPLICATION THEREOF

FIELD OF THE INVENTION

The invention belongs to the field of phytochemistry, relates to indole alkaloid compounds in a noni enzyme, and also relates to a preparation method thereof, and the application of indole alkaloid compounds in the noni enzyme.

BACKGROUND OF THE INVENTION

Alkaloids are a type of nitrogen-containing alkaline organic compounds that exist in nature (mainly plants, but some also exist in animals). They have alkali-like properties, so they were also called pseudoalkaloids in the past. Most of them have a complex ring structure, and the nitrogen is mostly contained in the ring; the nitrogen has significant biological activity and is one of the important effective ingredients in Chinese herbal medicine.

Many alkaloids can play a role in curing diseases. For example, the berbine in the rhizome of golden thread is the main component of berberine, which has antibacterial and anti-inflammatory effects, and is very effective for acute and chronic inflammation of the gastrointestinal tract. Some alkaloids have analgesic effects.

Noni is a relatively unknown fruit in the South Pacific, but has a medical effect. Noni has been used in Polynesia, China, India and other regions for more than two thousand years. Just like a aloe, a seaweed, a papaya, a tribulus and other plants, the noni has been proven to improve many different health conditions of humanity. At present, the noni enzyme obtained from fermented noni fruits are mostly sold as nutritious foods. At present, the development of the noni enzyme for medicinal use is lacking.

SUMMARY OF THE INVENTION

In view of this, the present invention has conducted in-depth research on the noni enzyme, and extracted the indole alkaloid compounds in the noni enzyme and the preparation method and application thereof. The compounds are new compounds that are able to inhibit the activity of a α-glucosidase.

The technical solution of the present invention is realized as follows:

Provided is the indole alkaloid compound in the noni enzyme, the structural formula of which is as follows:

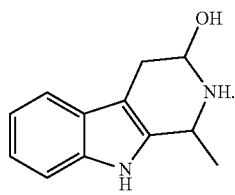

Provided is the indole alkaloid compound in the noni enzyme, the chiral structural formula of which is shown in formula (1):

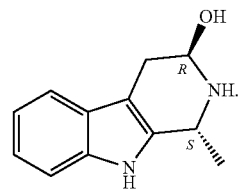

(1)

Provided is the indole alkaloid in the noni enzyme, the chiral structure of which is shown in formula (2):

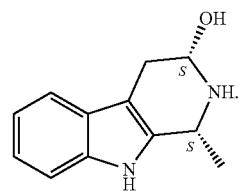

(2)

Provided is a method for preparing the indole alkaloid in the noni enzyme, which includes the following steps: extracting the noni enzyme with ethyl acetate; obtaining an organic phase and an aqueous phase; the aqueous phase being subjected to a column chromatography, a thin layer chromatography, and a molecular sieve chromatography in sequence; obtaining a target compound.

Further, a volume ratio of the said noni enzyme and the said ethyl acetate is 1:0.8 to 1.2.

Further, a volume ratio of the said noni enzyme and the said ethyl acetate is 1:1.

Further, conditions of the column chromatography are: using D201 chromatography column of macroporous resin; a ethanol-water mixed solvent with a ethanol volume percentage of 20-50% being as an eluent.

Further, a condition of the thin layer chromatography is: a methanol-chloroform mixed solvent with a methanol volume percentage of 10%-50% being used as a developing solvent, or a chloroform-acetone mixed solvent with an acetone volume percentage of 20%-25% being used as the developing solvent.

Further, conditions of molecular sieve chromatography are: the molecular sieve being Sephadex LH-20, and a chloroform-methanol mixed solvent with a chloroform volume percentage of of 0.01%-50% being used as the eluent.

The application of the indole alkaloid compound in the noni enzyme of the present invention in a preparation of an α-glucosidase inhibitor.

Compared with the prior art, the present invention has the beneficial effects that: provided are the indole alkaloid compounds with a new structure, which is able to inhibit the activity of the α-glucosidase, and also a method for preparing the said compound. The indole alkaloid compound in the noni enzyme provided by the invention has a simple preparation process, low cost and wide raw material sources.

DETAILED WAYS

Figure 1:
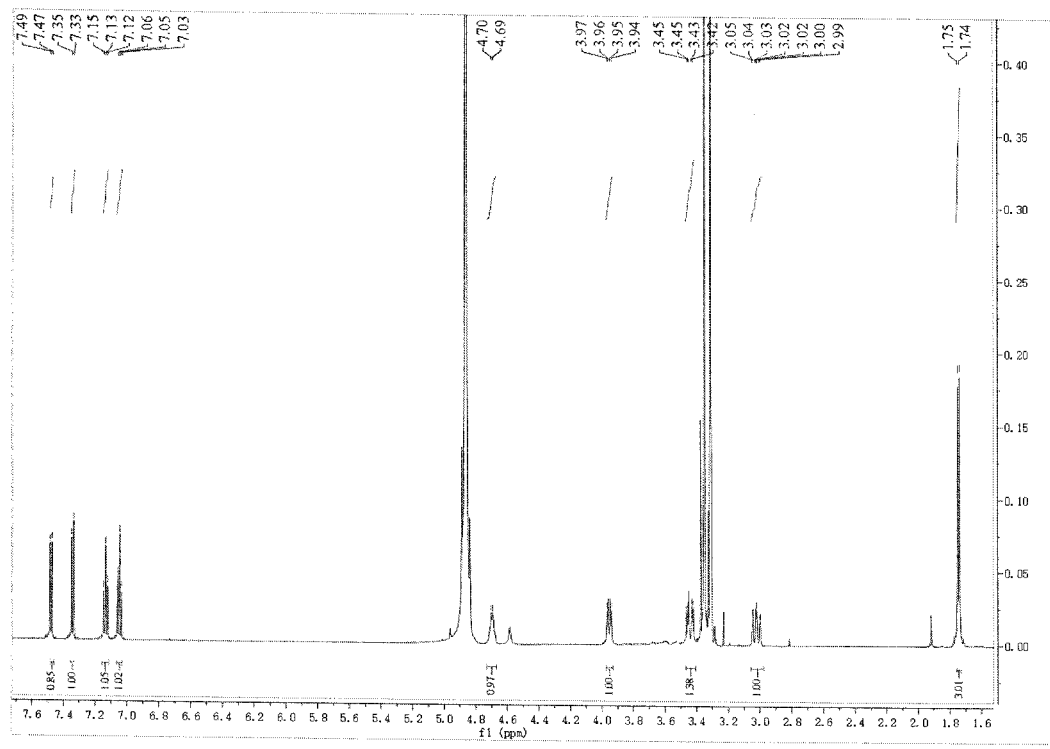
FIG. 1 shows H NMR of the compound 1.
Figure 2:
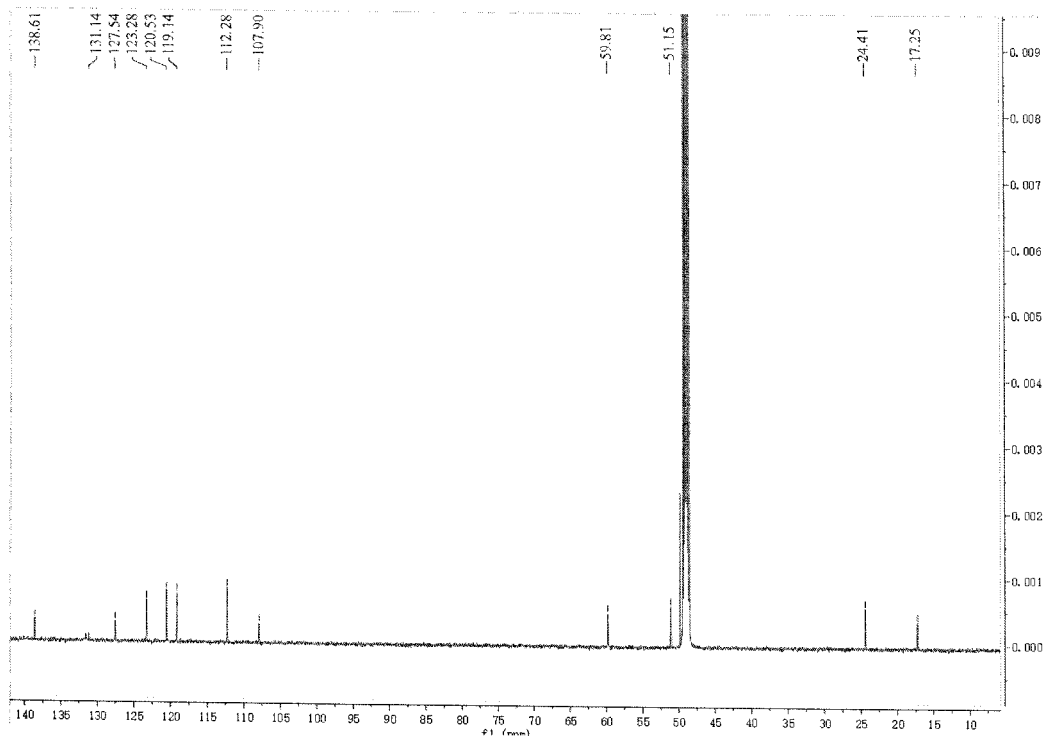
FIG. 2 shows $^{13}$C NMR of the compound 1.
Figure 3:
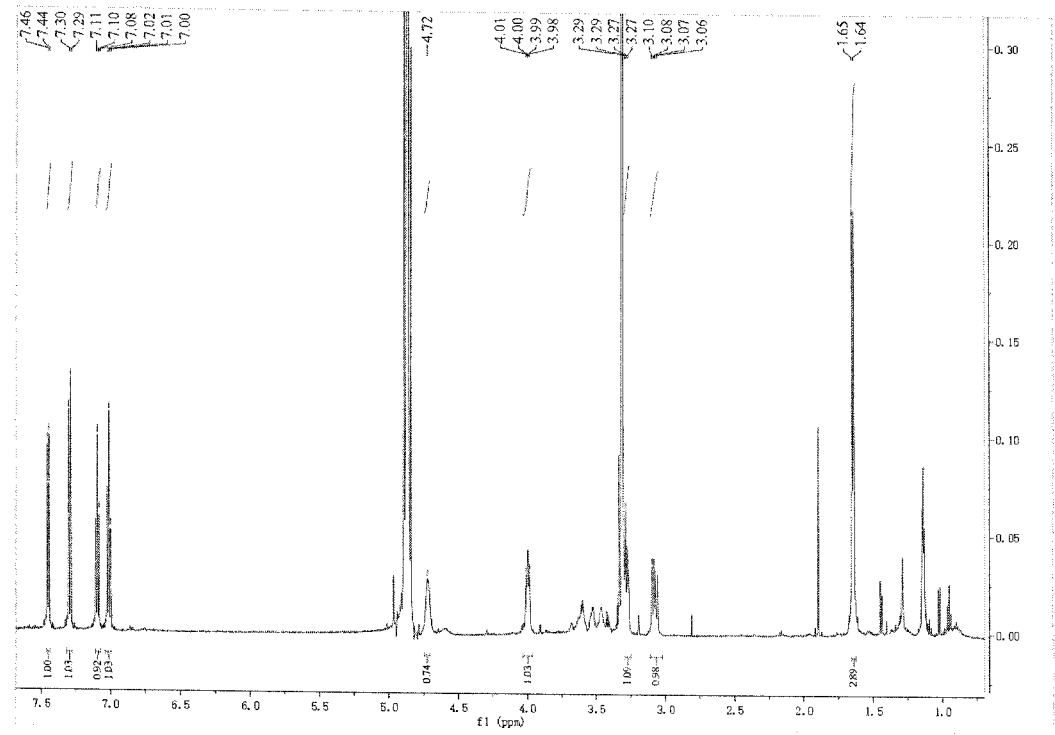
FIG. 3 shows H NMR of the compound 2.
Figure 4:
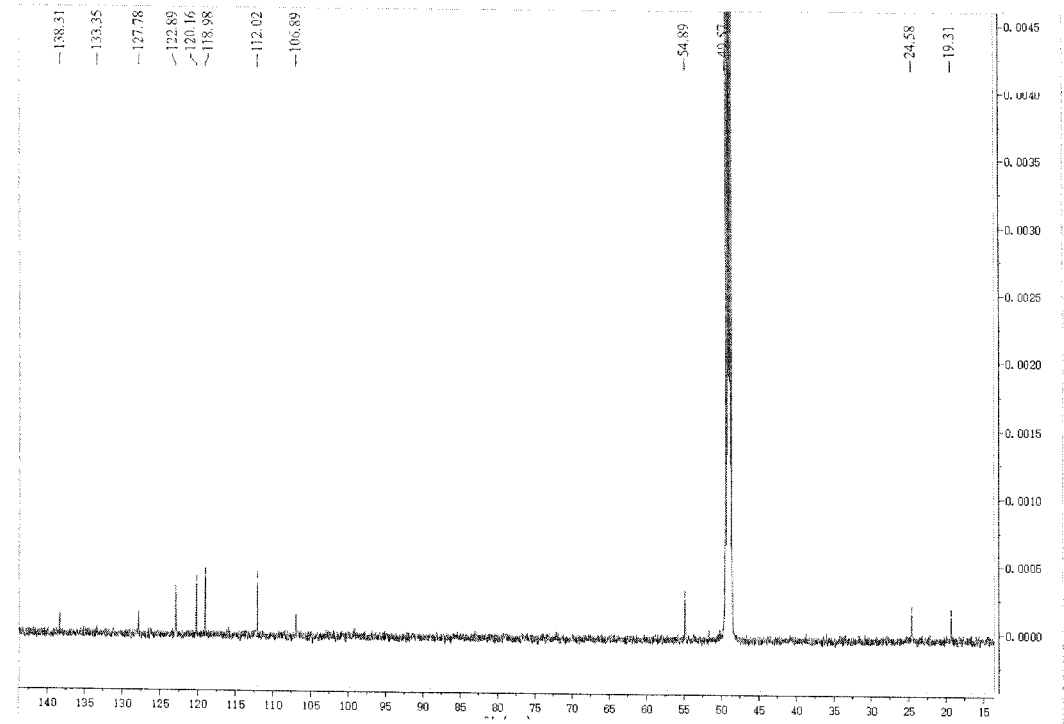
FIG. 4 shows $^{13}$C NMR of the compound 2.

According to the following embodiments, the present invention can be better understood. However, those skilled in the art can easily understand that the specific material ratios, process conditions and results described in the embodiments are only used to illustrate the present invention, and should not and will not limit the present invention described in detail in the claims.

The noni enzyme used in the present invention is a commercially available noni enzyme produced by Hainan Dazhoudao Noni Food Co., Ltd. The preparation method includes the following steps:
(1) cleaning the skin of mature noni fruit with a brush;
(2) cleaning the bottles, knives and cutting boards, and draining them for later use;
(3) taking out the noni fruit, draining the water, and slicing; put all the noni fruit slices according to a ratio of 1:3:10 (1 kg sugar: 3 kg noni fruit: 10 kg water) into a clean fermentation bottle (20 L white plastic bucket). About 20% of the space in the bottle is saved for fermentation;
(4) caping the bottle tightly and pasting the date of manufacture;
(5) During the fermentation of noni fruit, stirring after opening the bottle or shaking the bottle every day in the first month so as to soak fruit slices on the top layer into the liquid; in order to prevent the enzyme from alcoholization, adding a small amount of after a month or so;
(6) Fermenting in a cool place for three months, and then filtering to obtain the noni enzyme.

Embodiment 1

The preparation method of the indole alkaloid in the noni enzyme includes the following steps:

The noni enzyme and the ethyl acetate were mixed in a volume ratio of 1:1, and were extracted to obtain the organic phase and the aqueous phase. After the aqueous phase was concentrated, it was subjected to the column chromatography, the thin layer chromatography, and the molecular sieve chromatography in sequence; The conditions of the column chromatography are: the chromatographic column being a macroporous resin D201 column, and the ethanol-water mixed solvent with a ethanol volume percentage of 20% being used as the eluent; the condition of the thin layer chromatography is: the methanol-chloroform mixed solvent with a methanol volume percentage of 20% being as the developing solvent; the molecular sieve chromatography conditions are: the molecular sieve being the Sephadex LH-20, and the chloroform-methanol mixed solvent with a volume percentage of 50% chloroform being used as the eluent.

Obtaining the indole alkaloid compounds, respectively: Noni alkaloid C (1), Noni alkaloid D (2); the structural formulas are as follows:

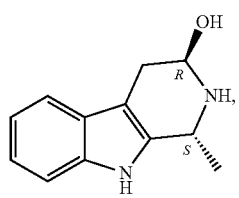

(1)

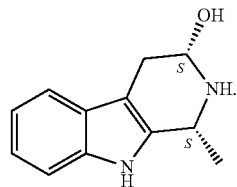

(2)

The compounds 1 and 2 are new compounds.

The physical and chemical properties, hydrogen spectrum and mass spectrometry detection data of each compound are as follows:

The compound 1 is a colorless crystal; easily soluble in water, methanol, DMSO; and a dark spot emerged under a 254 nm ultraviolet light. It is calculated by a HR-ESI-MS [m/z 225.1406, calculated value being 225.1465] that a molecular weight of the compound is 202, a molecular formula is $C_{12}H_{14}N_2O$, and a degree of unsaturation is 7. A $^1H$ NMR (400 MHz in DMSO) and a $^{13}C$ NMR (100 MHz in DMSO) are shown in the table.

| Position | $\delta_C$ | mult. | $\delta_H$ (J in Hz) | HMBC | $^1H$-$^1H$ COSY |
|---|---|---|---|---|---|
| 1 | | NH | | | |
| 2 | 131.1 | C | | | |
| 3 | 107.9 | C | | | |
| 3a | 127.5 | C | | | |
| 4 | 119.1 | C | | | 5 |
| 5 | 120.5 | CH | 4.8, t | 7, 3a | 4, 6 |
| 6 | 123.3 | CH | 4.8, t | | 5, 7 |
| 7 | 112.2 | CH | 5.6, d | | 6 |
| 7a | 138.6 | C | 5.2, d | | |
| 8 | 24.4 | $CH_2$ | 3.44, m | | 9 |
| | | | 3.01, m | | |
| 9 | 59.8 | CH | 3.2, 8.0, dd | 3, 11 | 8 |
| 10 | | NH | | | |
| 11 | 51.1 | CH | 4.8, 9.0, dd | 2, 3 | 12 |
| 12 | 17.4 | $CH_3$ | 4.4, d | 2 | 11 |

The compound 2 is a colorless crystal; easily soluble in water, methanol, DMSO; and a dark spot emerged under 254 nm ultraviolet light. It is calculated by the HR-ESI-MS [m/z 225.1406, calculated value being 225.1465] that a molecular weight of the compound is 202, a molecular formula is $C_{12}H_{14}N_2O$, and a degree of unsaturation is 7. The $^1H$ NMR (400 MHz in DMSO) and the $^{13}C$ NMR (100 MHz in DMSO) are shown in the table.

| Position | $\delta_C$ | mult. | $\delta_H$ (J in Hz) | HMBC | $^1H$-$^1H$ COSY |
|---|---|---|---|---|---|
| 1 | | NH | | | |
| 2 | 133.4 | C | | | |
| 3 | 107.0 | C | | | |
| 3a | 127.8 | C | | | |
| 4 | 119.0 | CH | | | 5 |
| 5 | 120.2 | CH | 4.8, t | 7, 3a | 4, 6 |
| 6 | 122.9 | CH | 4.8, t | | 5, 7 |
| 7 | 112.1 | CH | 5.6, d | | 6 |
| 7a | 138.3 | C | 5.2, d | | |
| 8 | 24.6 | $CH_2$ | 3.27, m | | 9 |
| | | | 3.07, m | | |
| 9 | 54.9 | CH | 3.8, 5.4, dd | 3, 11 | 8 |
| 10 | | NH | | | |
| 11 | 49.6 | CH | 2.4, 6.0, dd | 2, 3 | 12 |
| 12 | 19.3 | $CH_3$ | 4.4, d | 2 | 11 |

Embodiment 2

The preparation method of the indole alkaloid in the noni enzyme includes the following steps:

The noni enzyme and the ethyl acetate were mixed in a volume ratio of 1:0.8, and extracted to obtain the organic phase and the aqueous phase. The aqueous phase was concentrated and then subjected to the column chromatography, the thin layer chromatography, and the molecular sieve chromatography; The conditions of the column chromatography are: the chromatographic column being the macroporous resin D201 column, and the ethanol-water mixed solvent with a ethanol volume percentage of 30% being used as the eluent; the condition of the thin layer chromatography is: the methanol-chloroform mixed solvent with a methanol volume percentage of 10% being as the developing solvent; the molecular sieve chromatography conditions are: the molecular sieve being Sephadex LH-20, and the chloroform-methanol mixed solvent with a chloroform volume percentage of 1% being used as the eluent.

Two indole alkaloid compounds in the noni enzyme were obtained, and the detection was consistent with the embodiment 1.

Embodiment 3

The preparation method of the indole alkaloid in the noni enzyme includes the following steps:

The noni enzyme and the ethyl acetate were mixed in a volume ratio of 1:1.2, and extracted to obtain the organic phase and the aqueous phase. After the aqueous phase was concentrated, it was subjected to the column chromatography, the thin layer chromatography, and the molecular sieve chromatography in sequence; The column chromatography conditions are: the chromatographic column being the macroporous resin D201 column, and the ethanol-water mixed solvent with a ethanol volume percentage of 50% being used as the eluent; the thin layer chromatography condition is: the methanol-chloroform mixed solvent with a methanol volume percentage of 50% being as the developing solvent; the molecular sieve chromatography conditions are: the molecular sieve being Sephadex LH-20, and the chloroform-methanol mixed solvent with a chloroform volume percentage of 10% being used as the eluent.

Two indole alkaloid compounds in the noni enzyme were obtained, and the detection was consistent with the embodiment 1.

Embodiment 4

The difference between this embodiment and the embodiment 1 lies in that the thin layer chromatography condition is: the chloroform-acetone with a volume ratio of 4:1 being as the developing solvent. Two indole alkaloid compounds in the noni enzyme were obtained, and the detection was consistent with the embodiment 1.

Example 5

The difference between this embodiment and the embodiment 1 lies in that the thin layer chromatography condition is: the chloroform-acetone with a volume ratio of 3:1 being as the developing solvent. Two indole alkaloid compounds in the noni enzyme were obtained, and the detection was consistent with the embodiment 1.

Test Example 1

The $\alpha$-glucosidase, also known as a glucosyltransferase (EC.3.2.1.20), is systemically named as a $\alpha$-D-glucoside glucohydrolase. It has dual functions of hydrolysis and transglycosidation in the catalytic reaction of sugar. Hydrolysis can cleave a $\alpha$-1,4 glycosidic bond from non-reducing ends of a $\alpha$-glucoside, a oligosaccharide and a glucan to release a glucose; a $\alpha$-glucosidase inhibitor can inhibit the $\alpha$-glucosidase of a brush border of a small intestine mucosa to delay the absorption of carbohydrates and reduce postprandial hyperglycemia.

According to the testing, the inhibitory activity of the compound 1 of the present invention on $\alpha$-glucosidase is 4.109 mmol/ml, and the inhibitory activity of the compound 2 on $\alpha$-glucosidase is greater than 6 mmol/ml. Both compounds can be applied to the preparation of the $\alpha$-glucosidase inhibitor.

We claim:

1. A preparation method for indole alkaloid compounds from a noni enzyme, wherein the preparation method comprises the following steps: extracting the noni enzyme with an ethyl acetate; obtaining an organic phase and an aqueous phase; the aqueous phase being subjected to a column chromatography, a thin layer chromatography, and a molecular sieve chromatography in sequence; obtaining a compound thereof;

wherein a chiral structural formula of each of the indole alkaloid compounds is shown in formula (1) or (2):

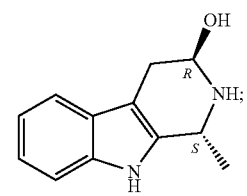

(1)

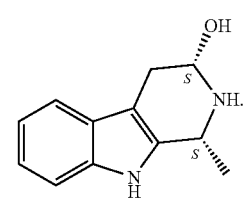

(2)

2. The preparation method according to claim 1, wherein a volume ratio of the noni enzyme and the ethyl acetate is 1:0.8-1.2.

3. The preparation method according to claim 1, wherein the volume ratio of the noni enzyme and the ethyl acetate is 1:1.

4. The preparation method according to claim 1, wherein conditions of the column chromatography are: using a D201 chromatography column of macroporous resin, and an ethanol-water mixed solvent with an ethanol volume percentage of 20-50% is an eluent.

5. The preparation method according to claim 1, wherein: a condition of the thin layer chromatography is: a methanol-chloroform mixed solvent with a methanol volume percentage of 10%-50% being used as a developing solvent, or a chloroform-acetone mixed solvent with an acetone volume percentage of 20%-25% being used as the developing solvent.

6. The preparation method according to claim 1, wherein: conditions of the molecular sieve chromatography are: a chloroform-methanol mixed solvent with a chloroform volume percentage of 0.01%-50% being used as an eluent.

* * * * *